United States Patent [19]
Py

[11] Patent Number: 5,163,929
[45] Date of Patent: Nov. 17, 1992

[54] OCULAR VIAL

[75] Inventor: Daniel Py, Short Hills, N.J.

[73] Assignee: O.P.T.I.C., Inc., N.J.

[21] Appl. No.: 601,944

[22] Filed: Oct. 22, 1990

Related U.S. Application Data

[62] Division of Ser. No. 322,761, Mar. 13, 1989, Pat. No. 5,085,651.

[51] Int. Cl.⁵ ............................................ A61M 35/00
[52] U.S. Cl. ..................... 604/298; 604/294; 604/295
[58] Field of Search ............... 604/294-302, 604/131-137; 222/420

[56] References Cited

U.S. PATENT DOCUMENTS

| | | | |
|---|---|---|---|
| 2,534,310 | 12/1950 | Silverman | 222/420 |
| 2,698,015 | 12/1954 | Brown | 128/233 |
| 3,170,462 | 2/1965 | Hall | 604/298 X |
| 3,261,355 | 7/1966 | Burbig | 604/296 |
| 3,934,585 | 1/1976 | Maurice | 128/225 |
| 4,052,985 | 10/1977 | Coleman et al. | 604/301 |
| 4,111,200 | 9/1978 | Sbarra et al. | 604/298 |
| 4,175,704 | 11/1979 | Cohen | 239/230 |
| 4,398,909 | 8/1983 | Portnoff | 604/295 |
| 4,573,506 | 3/1986 | Paoletti | 141/98 |
| 4,573,982 | 3/1986 | Forbes et al. | 604/300 |
| 4,623,337 | 11/1986 | Maurice | 604/298 X |
| 4,750,650 | 6/1988 | Ling | 604/296 X |
| 4,755,169 | 7/1988 | Sarnoff et al. | 604/136 |
| 4,758,237 | 7/1988 | Sacks | 604/294 |
| 4,792,334 | 12/1988 | Py | 604/295 X |
| 4,871,094 | 10/1989 | Gall et al. | 222/386 |
| 4,927,062 | 5/1990 | Walsh | 604/295 X |
| 5,085,651 | 2/1992 | Py | 604/294 X |

OTHER PUBLICATIONS

Wheaton Catalog, p. 21.

*Primary Examiner*—David Isabella
*Assistant Examiner*—Elizabeth M. Burke
*Attorney, Agent, or Firm*—Kenyon & Kenyon

[57] ABSTRACT

An ocular treatment apparatus for applying medicament into an eye has a vial defining a vial cavity for holding medicament. A nozzle is attached over an opening in the vial and is in fluid communication with the vial cavity for releasing drops of medicament. A piston member is suspended within the vial and slideably engaged within the vial cavity for displacing a substantially predetermined volume of medicament through the nozzle for release into the eye.

16 Claims, 6 Drawing Sheets

OCULAR VIAL

This application is a division, of U.S. patent application Ser. No. 07/322,761 now U.S. Pat. No. 5,085,607 filed Mar. 13, 1989.

FIELD OF THE INVENTION

The invention is directed to ocular treatment apparatus and, more particularly, to ocular treatment apparatus for applying drops of medicament into an eye.

BACKGROUND INFORMATION

Known devices for applying drops of medicament into an eye typically comprise a flexible vial containing the medicament and a nozzle attached over an opening of the vial for releasing drops of medicament into the eye. In some known devices the nozzle comprises a relatively long and narrow tip, referred to by those skilled in the art as an ocumeter. The ocumeter is generally provided to increase the user's control over the size of each drop and the number of drops released from the vial. Drops are applied to the eye by pointing the nozzle toward the open eye and squeezing the vial to release one or more drops of medicament into the eye.

Other known devices store the medicament in a vial and employ a separate eyedropper to release the drops of medicament into the eye. Eyedroppers typically comprise a small tube having a nozzle formed on one end and a suction bulb attached to the other end. The medicament is drawn into the tube by squeezing the suction bulb and inserting the tube into the vial. The suction bulb is then released to draw the medicament into the tube. Drops of medicament are applied to the eye by pointing the tube toward the eye and squeezing the suction bulb to release the drops of medicament into the eye.

People frequently encounter difficulty in applying eyedrops with these known devices. For example, many people have poor vision and/or their hands may shake and, thus, they have difficulty handling small eyedroppers. This can be especially dangerous if the user accidentally touches the cornea of the eye with the tip of the eyedropper. The cornea is an extremely sensitive area and can be easily damaged. Moreover, elderly people frequently have arthritis or other ailments disabling their fingers so that it can be extremely painful, and in some cases impossible, for these people to squeeze a device to release the eyedrops. This problem is especially critical with ocumeter devices because the impedance to fluid flow created by the ocumeter requires a greater squeezing force on the vial than with other devices. As a result, the users usually cannot accurately control the way they squeeze the vial or dropper and force too many drops through the nozzle. Likewise, because the users have difficulty squeezing the vial or dropper, they have trouble aiming the eyedrops into their eyes. Accordingly, in many instances, the degree of ophthalmologic patient compliance with such known devices is unacceptably low.

The maximum volume of liquid medicament that should be introduced into an eye at one time is about 25 microliters. Any amount greater usually spills over the eyelid and onto the person's cheek. Accordingly, another problem associated particularly with devices employing an eyedropper or squeeze vial is that both the volume of the drops, and the number of drops released from such devices cannot be accurately controlled. If the vial or eyedropper is squeezed with too much force, the volume of each drop may well exceed 25 microliters and, frequently, more than one drop is squeezed through the nozzle. Known vials often release drops larger than 30 microliters. As a result, medicament frequently drips onto the person's cheek and, depending upon the type of medicament, it may irritate the person's skin. Moreover, if the eye receives too large a drop or several drops, the eye may be subjected to an overdose of medicament. This condition can be extremely dangerous, especially if the patient is particularly sensitive to the medicament. For example, in some patients an overdose of beta blockers may cause severe side effects, such as bronchospasma or lowering of the heart rate, and may possibly cause death.

Another problem with known devices employing a squeeze vial or an eyedropper is that the medicament within the vial can easily become contaminated. Frequently people accidentally touch the conjunctiva of the eye with the tip of the vial or eyedropper. If the conjunctiva is infected, the tip of the nozzle can pick up the germs and contaminate the medicament that is squeezed into the tip. After the squeezing force is released from the device, the suction frequently draws medicament back into the device that was contaminated by contact with the tip. This problem is especially critical with devices employing ocumeters. The long and narrow tip of an ocumeter is more likely to accidentally touch the conjunctiva. Also, an ocumeter has a large volume of space, often referred to as "dead space," that holds medicament that is squeezed into the tip, but is not released into the eye. The medicament within the dead space, therefore, contacts the contaminated tip and, in turn, can contaminate the remainder of the medicament within the vial. This problem is exacerbated when the preservatives within the medicament, or the medicament itself, cannot destroy the particular germs or prevent repetitive contamination by the germs. Further use of the contaminated medicament may then only maintain or provoke a recurrence of the contaminating infection in the eye. This problem is especially critical shortly after eye surgery, for example, a corneal transplant, when the treated eye is most susceptible to infection.

Another problem with squeeze vials or eyedroppers is that the suction may force air bubbles into the drops of medicament. The air bubbles decrease the amount of medicament in each drop, and, accordingly, decrease the effectiveness of the treatment.

Yet another problem with known ocular treatment devices is that they are generally difficult to use with medicaments that must be mixed from two separate compounds or solutions shortly prior to use. For example, some medicaments require that two separate liquid solutions be mixed prior to use while, on the other hand, others require that a powder or other solid phase medicament be mixed with a liquid solvent prior to use. These medicaments usually cannot be premixed by the manufacturer because their shelf life after mixing is too short. When employing known devices, such medicaments are generally mixed by the user who is required to pour or stir one solution into the other, and then shake or stir the mixture to form a homogeneous solution. Frequently, elderly people have difficulty mixing the solutions because their hands may shake. As a result, they often spill part of one solution and do not obtain a proper mixture of medicament. Likewise, this procedure is confusing to many people because the user is required to first measure and then mix two separate solutions.

It is an object of the present invention, therefore, to provide an ocular treatment apparatus that overcomes the problems and disadvantages of known devices, and to provide an improved apparatus for applying medicament into an eye.

SUMMARY OF THE INVENTION

The present invention is directed to an ocular treatment apparatus for applying medicament into an eye. The ocular apparatus comprises a nozzle defining an orifice for releasing medicament into the eye. Storage means of the apparatus are in fluid communication with the nozzle orifice for holding medicament for release into the eye. The ocular apparatus further includes displacement means for displacing a substantially predetermined volume of medicament within the storage means through the nozzle orifice for release into the eye.

The storage means of the apparatus preferably includes a nozzle cavity formed within the nozzle and in fluid communication with the nozzle orifice. The displacement means preferably includes a piston member engageable within the nozzle cavity for displacing medicament within the cavity through the nozzle orifice for release into the eye.

The present invention is also directed to another embodiment of an ocular treatment apparatus for applying medicament into an eye. The ocular apparatus comprises a vial defining a cavity for holding medicament. The vial has formed therein an orifice in fluid communication with the cavity for releasing medicament from the vial. A piston member of the apparatus is moveable within the vial for displacing a substantially predetermined volume of medicament from the cavity, through the orifice, for release into the eye. The vial preferably further defines a second cavity in fluid communication with the first cavity and with the nozzle orifice. The piston member is engageable within the second cavity for displacing fluid within the second cavity, through the orifice, for release into the eye.

In a further embodiment of the present invention, the vial of the apparatus comprises an exterior wall having a generally cylindrical surface, and an interior wall, also having a generally cylindrical surface. The interior wall extends within the exterior wall from a closed end of the vial. The other end of the interior wall defines a closed end joined to the piston member. The interior wall is moveable relative to the exterior wall to depress the piston member, for displacing medicament through the orifice for release into the eye.

In yet another embodiment of the invention, an ocular treatment apparatus is provided for applying medicament into an eye. The ocular apparatus comprises a nozzle having an orifice defined therein for releasing medicament into the eye. Storage means of the apparatus are in fluid communication with the nozzle orifice for holding medicament for release into the eye. The apparatus further includes a vial defining a first cavity for holding a first medicament in fluid communication with the storage means. The vial also defines a second cavity for holding a second medicament. The ocular apparatus further includes means for controllably placing the first vial cavity in fluid communication with the second vial cavity, for mixing the first and second medicaments into a mixed medicament solution. Displacement means of the apparatus are provided for displacing a substantially predetermined volume of mixed medicament within the storage means, through the nozzle orifice, for release into the eye. In yet another embodiment of the apparatus, either the first cavity or second cavity of the vial is evacuated to a subatmospheric pressure. When the first and second medicaments are mixed, the pressure differential between the first and second cavities facilitates the mixing of the separate medicament solutions.

In a further embodiment of the invention, the storage means includes a nozzle cavity defined within the nozzle and in fluid communication with both the nozzle orifice and the first vial cavity. The displacement means also comprises a piston member, engageable within the nozzle cavity, for displacing medicament in the nozzle cavity through the nozzle orifice for release into the eye. The vial of the apparatus also preferably includes an inner shell and an outer shell. The inner shell is connected to the outer shell and moveable within the outer shell. The outer shell defines the first vial cavity for holding a first medicament, and the inner shell defines the second vial cavity for holding a second medicament. The piston member is joined to the inner shell, and engageable within the nozzle cavity, by depressing the inner shell relative to the outer shell. The piston member then displaces medicament within the nozzle cavity through the nozzle orifice, for release into the eye.

One advantage of the ocular treatment apparatus of the present invention over known devices is that the apparatus displaces a substantially predetermined volume of medicament for release into the eye. Each time the apparatus is employed, a single drop of medicament, having a substantially predetermined volume, may be released into the eye. The apparatus of the invention may also be employed to contain two separate medicament solutions. Both solutions are contained separately within the apparatus. The separate solutions can then be mixed within the apparatus into one homogeneous medicament solution, immediately prior to releasing drops of medicament into the eye, without requiring the user to measure and/or pour one solution into the other.

Other objects and advantages of the invention will become apparent in view of the following detailed description, and drawings taken in connection therewith.

DETAILED DESCRIPTION

Figure 1:
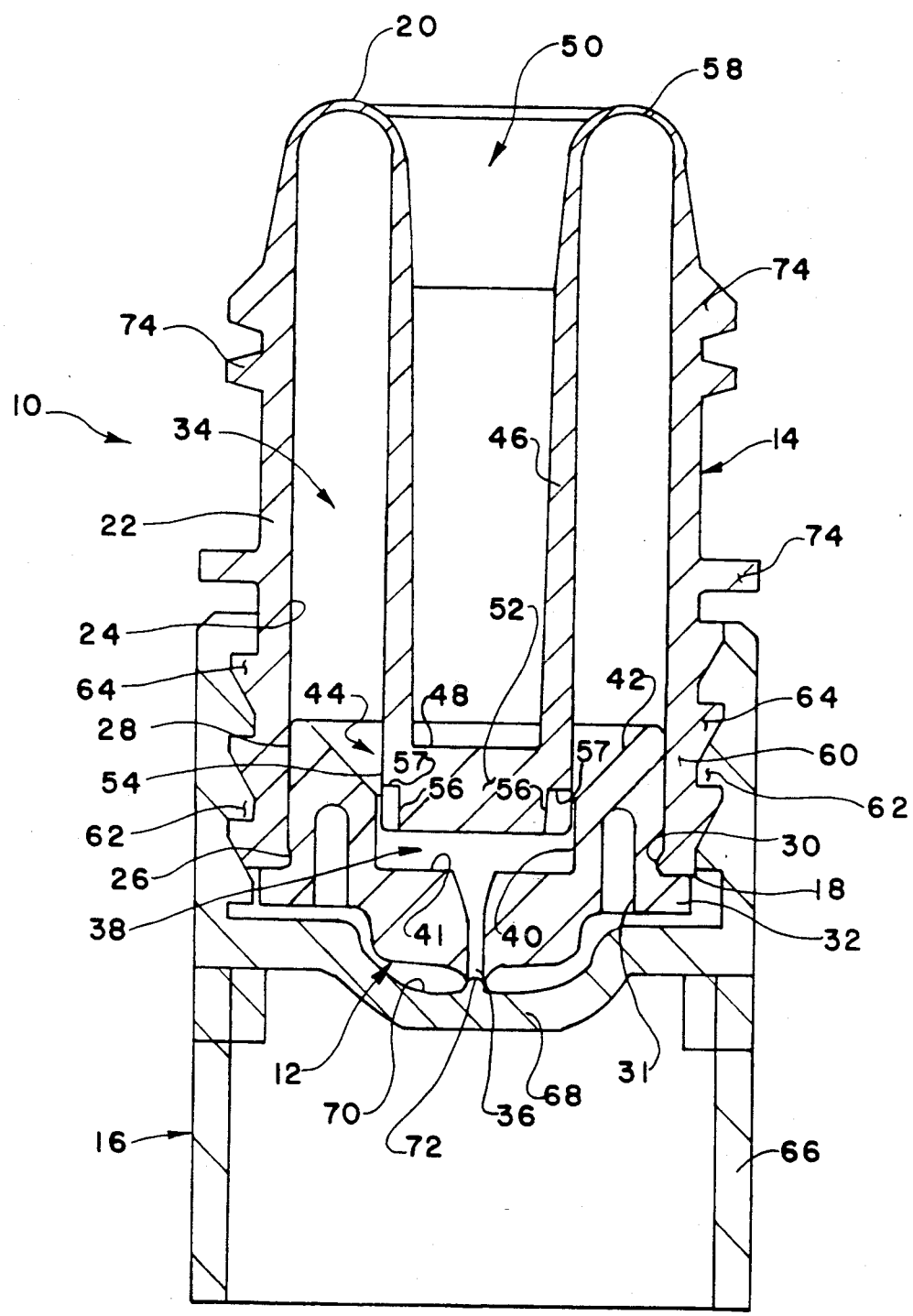
FIG. 1 is a cross-sectional view of an ocular treatment apparatus embodying the invention.

In FIG. 1 an ocular treatment apparatus embodying the invention is generally indicated by the reference numeral 10. The ocular apparatus 10 generally includes a nozzle member 12, a body 14, and a cap 16. These components are preferably molded from a suitable plastic, such as low density polyethylene.

The body 14 of the apparatus defines an open end 18, an annular shaped end 20, and an exterior wall 22 having a substantially cylindrical interior surface 24. A lobe 26 of the body is formed adjacent the edge of the open end 18 on the interior surface 24, for connecting the nozzle member 12 to the body 14, as will be described further below.

The nozzle member 12 includes a substantially cylindrical surface 28 which, as shown in FIG. 1, is dimensioned to slideably fit within the interior surface 24 of the body 14. The cylindrical surface 28 has formed therein a peripheral recess 30 dimensioned to receive the lobe 26 of the body 14. The nozzle member 12 further defines a cylindrical recess 31, formed within an exterior face of the nozzle member, and extending in the axial direction thereof a distance beyond the recess 26.

A flange 32 of the nozzle member is formed adjacent the recess 30 and has an outer diameter larger than the diameter of the interior surface 24 of the body. The nozzle member 12 is connected to the body 14 by sliding the cylindrical surface 28 through the lobe 26 until the lobe 26 snaps into the recess 30. The lobe 26 and recess 30 form a substantially fluid tight seal between the nozzle member and the body. The recess 31 allows the surface 28 to flex inwardly to fit through the lobe 26. The flange 12 is seated against the open end 18 of the body and, thus, prevents the nozzle member 12 from being forced any further into the body 14. Because the body 14 and nozzle member 12 are made of flexible plastic material, they provide the flexibility required to be pressed and snapped together. When the nozzle member 12 and body 14 are assembled, they form a closed fluid cavity, indicated generally as 34, for holding medicament. The cavity 34 is preferably filled with medicament before the nozzle member 12 is assembled to the body 14. The nozzle member is then snapped into the body, as shown in FIG. 1, forming a substantially fluid tight seal for holding the medicament.

The nozzle member 12 further defines a nozzle orifice 36 extending through the nozzle member in its axial direction. A drop cavity 38 of the nozzle member, defined by a substantially cylindrical interior surface 40, and flat base surface 41, is in fluid communication with the nozzle orifice 36. As shown in FIG. 1, the diameter of the nozzle orifice 36 increases in the axial direction of the nozzle member so as to flare open into the drop cavity 38. The flared opening in the nozzle orifice 36 induces the flow of medicament therethrough. The nozzle member 12 further defines a sloped surface 42 which slopes inwardly from the edge of the cylindrical surface 28 to the drop cavity 38. The slope of the surface 42 induces the flow of medicament into the drop cavity.

The ocular apparatus 10 further includes displacement means for displacing a substantially predetermined volume of medicament through the nozzle orifice 36. The displacement means comprises a piston member indicated generally as 44. The piston member 44 is formed partly by an interior wall 46 of the body 14, extending inwardly from the annular end 20 of the body, and along a substantial portion of its axial length. The end of the wall 46 opposite the annular end 20 of the body is formed into a flat, closed end 48. As shown in FIG. 1, the interior wall 46 thus defines an open cavity 50 within the body 14. The closed end 48 is formed into a piston head 52 having a substantially cylindrical surface 54 which, as shown in FIG. 1, is dimensioned to be slideably engaged within the cylindrical surface 40 of the drop cavity 38. The piston head 52 preferably defines several axially elongated grooves, shown typically as 56, 56, formed within the cylindrical surface 54. Each groove 56, 56 extends upwardly from the base of the piston head and defines a closed end 57, 57.

As shown in FIG. 1, the annular end 20 of the body defines a wall 58 having a thinner cross section than either of the walls 22 or 46. The wall 58 flexes inwardly to permit the piston member 44 to be depressed toward the drop cavity 38. When the piston member is depressed, the piston head 52 is forced into the drop cavity to displace the medicament therein through the orifice 36 for release into the eye, as will be described further below.

In FIG. 1 the piston member 44 is shown partially depressed into the drop cavity 38. Before the piston member 44 is depressed, however, the base of the piston head 52 is normally located above the drop cavity 38 and adjacent the sloped surface 42. In this way, medicament fills the drop cavity 38 by flowing over the surface 42 and below the base of the piston head 52. When the piston member 44 is initially depressed, as shown in FIG. 1, air within the drop cavity, and some medicament, is forced by the piston head 52 upwardly between the grooves 56, 56 and the cylindrical surface 40, and into the cavity 34. However, when the piston member 44 is depressed far enough so that the closed ends 57, 57 of the grooves are moved into the drop cavity, the medicament in the drop cavity cannot flow back into the cavity 34, but can only flow through the orifice 36 for release into the eye. As would be evident to one skilled in the art, the grooves 57, 57 could likewise be formed within the cylindrical surface 40 of the drop cavity 38 to serve the same purpose. Because the piston member 44 initially forces the air within the drop cavity back into the cavity 34, the apparatus 10, as opposed to known ocular apparatus, minimizes the risk of forcing any air bubbles into a drop of medicament.

The displacement means of the invention thus accurately controls the volume of each drop of medicament, and the number of drops of medicament released from the ocular apparatus. Each time the apparatus is employed, a single drop of medicament may be released into the eye. The volume of each drop is controlled by appropriately dimensioning the drop cavity 38 and the piston member 44. Accordingly, the volume of each drop is equal to the volume of medicament contained within the drop cavity 38 below the piston head 52, when the piston head is depressed far enough so that the closed ends 57, 57 of the grooves are moved immediately below the opening of the drop cavity. Because it is desirable to have about a 20 microliter drop, as described above, this volume is preferably equal to about 20 microliters.

In operating the apparatus 10, a person aims the nozzle orifice 36 toward the open eye and presses lightly on the annular end 20 with a finger, to depress the piston member 44. The base of the piston head 52 is then pressed against the bottom surface 41 of the drop cavity 38, and a 20 microliter drop of medicament is displaced through the orifice 36 for release into the eye. As can be seen, each time the piston member 44 is depressed only one 20 microliter drop of medicament is released. Thus, unlike other known devices, the apparatus of the invention releases a substantially predetermined volume of medicament. Moreover, because only a slight force is required to depress the piston member, even people with arthritic fingers can more accurately release a drop of medicament. When the downward pressure is released from the piston member 44, the tension in the wall 58, which is flexed inwardly when the piston member is depressed, pulls the wall 58 back into its initial shape and, thus, drives the piston head 52 upwardly to its normal position above the drop cavity 38. Medicament then flows from the cavity 34, beneath the piston head 52, and into the drop cavity 38 until the cavity becomes filled again. The surface tension and viscosity of the medicament, and the small diameter of the orifice 36, generally prevents the medicament from leaking through the orifice 36, unless it is forced through the orifice by the piston member 44. Another 20 microliter drop of medicament can then be released through the orifice 36 by depressing the piston member 44.

As shown in FIG. 1, the volume of the nozzle orifice 36 or, that is, the dead space, is relatively slight, especially in comparison to known ocumeter devices. Therefore, in the event that the nozzle orifice does become contaminated, only a small volume of medicament will contact the germs within the orifice. Accordingly, the risk of contaminating the rest of the medicament within the vial is reduced. Moreover, because the nozzle orifice is not formed within an extended tip as, for example, the tip of an ocumeter device or eyedropper, the user will likely not accidentally touch an infected conjunctiva with the nozzle and contaminate the apparatus.

The cap 16 of the ocular apparatus 10 is provided to cover the nozzle orifice 36 when the apparatus is not in use. The cap 16 comprises a threaded portion 60 having formed therein threads 62, 62 which, as shown in FIG. 1, are dimensioned to mate with threads 64, 64 formed on the outer surface of the body 14. The cap 16 further comprises a handle portion 66 provided to grip the cap and thread it onto the body 14. An interior wall 68 of the cap extends across the cap between the threaded portion 60 and handle portion 66. The center portion of the wall 68 is formed into a recessed surface 70, dimensioned to fit around the nozzle member 12 when the cap 16 is threaded onto the body 14. The cap 16 further includes a nipple 72 formed on the surface 70 on the axial center of the cap. The nipple 72 is dimensioned to fit into the orifice 36 of the nozzle member to block the flow of fluid therethrough. When the cap 16 is threaded onto the body 14, the nipple 72 of the cap is rotated into the orifice 36 and thus closes the orifice. The cap 16 therefore prevents any medicament from leaking from the orifice, or prevents any foreign particles from entering the nozzle orifice and contaminating the medicament within the apparatus.

The apparatus 10 further includes several peripheral flanges 74, 74 formed on the exterior surface of the wall 22 and provided to mount the apparatus to other ocular devices for applying medicament into an eye. For example, other devices may be employed to properly orient the apparatus 10 over the eye and/or evert the lower eyelid when a drop of medicament is released into the eye. One such device is disclosed in a co-pending U.S. patent application No. 07/267,526, filed Nov. 4, 1988 in the name of Daniel Py, entitled "Ocular Treatment Apparatus", which is a continuation-in-part of U.S. patent application No. 07/118,388, filed Nov. 6, 1987, now U.S. Pat. No. 4,792,334, issued Dec. 20, 1988, which are both hereby expressly incorporated by reference as part of the present disclosure. The apparatus 10 may be used instead of the vial disclosed in the above-referenced co-pending application. As will be evident to those skilled in the art, the displacement member disclosed in that application is dimensioned to fit within the cavity 50 of the apparatus 10, to depress the piston member 44 and, in turn, release a single drop of medicament into the eye. One advantage of using the apparatus 10 with other such devices is that the nozzle of the apparatus 10 cannot come into contact with an infected conjunctiva because it is mounted within the device above the eye. Accordingly, the risk of contaminating the medicament within the apparatus is further reduced.

Figure 2:
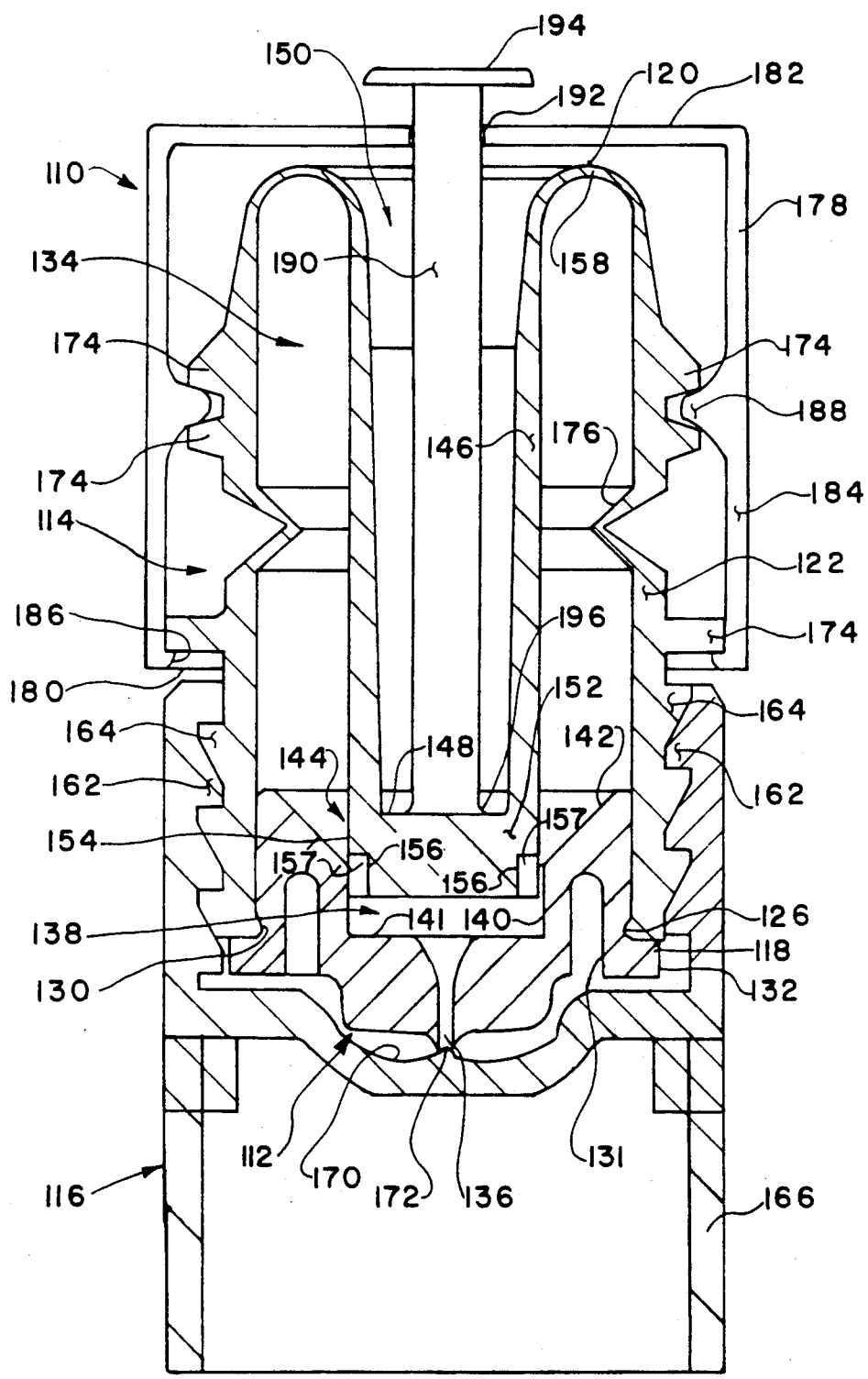
FIG. 2 is a cross-sectional view of a second embodiment of an ocular treatment apparatus embodying the invention.

Turning to FIG. 2, another embodiment of the ocular treatment apparatus of the invention is generally indicated by the reference numeral 110. The apparatus 110 is substantially similar to the apparatus 10 described above in relation to FIG. 1. Accordingly, the elements of the apparatus 110 are referenced with the same numbers as the like elements of the apparatus 10, except to include the prefix 1. For example, the body 14 of the apparatus 10 shown in FIG. 1 is the same as the body 114 of the apparatus 110 shown in FIG. 2. Likewise, because many of the elements of the apparatus 110 are the same as the corresponding elements of the apparatus 10, only those elements that are new or different will be hereinafter described.

The apparatus 110 comprises a drop cavity 138 having a base 141. As shown in FIG. 2, the base 141 is slanted with respect to the longitudinal axis of the apparatus. Likewise, the base of the piston head 152 is slanted at the same angle as the base 141 so that when the piston member 144 is fully depressed, the surfaces of the base 141 and piston head 152 completely engage. The slanted configuration of the piston head 152 and base 141 are provided generally for use with relatively viscous medicaments in order to induce the flow of such medicaments through the orifice 136. The apparatus 110 further comprises an accordion section 176, formed within the wall 122, and located between the peripheral flanges 174, 174. The accordion section 176 provides the body 114 with additional flexibility for depressing the piston member 144.

The apparatus 110 also includes a cover 178 which is provided for holding the apparatus when releasing drops of medicament. The cover 178 comprises an open end 180, a closed end 182, and a generally cylindrical shaped wall 184. A first peripheral lobe 186 of the cover is formed, adjacent the open end 180 on the interior surface of the wall 184. A second peripheral lobe 188 of the cover is also formed on the interior surface of the wall 184, between the first lobe 186 and closed end 182. The first and second peripheral lobes, 186 and 188, respectively, are provided to connect the cover 178 to the body 114. As shown in FIG. 2, the first lobe 186 is snapped over the flange 174 of the body, and the second lobe 188 is, in turn, snapped into the space between the other flanges 174, 174.

The apparatus 110 further includes a piston rod 190 which is mounted within the cover 178 to depress the piston member 144 and, thus, release drops of medicament from the apparatus. The piston rod 190 is dimensioned to fit through an opening 192 which, as shown in FIG. 2, is formed in the axial center of the closed end 182 of the cover. The piston rod 190 includes a button 194 on one end, and is abutted on its other end 196 against the surface 148 of the piston member.

In the operation of the apparatus 110, the piston member 144 is depressed to release a substantially predetermined volume of medicament by pushing the button 194 toward the cover 178. The piston rod 190, in turn, drives the piston head 152 into the drop cavity 138 and against its base 141, and thus displaces the medicament within the drop cavity through the orifice 136. When the button 194 is released, the tension in the wall 158, which is bent inwardly when the piston member is depressed, and the spring force in the accordion section 176, which is compressed when the piston member is depressed, drives the piston member 144 upwardly into its initial position above the drop cavity 138. The button 194 may then be pressed into the cover 178 to release another drop of medicament.

Figure 3:
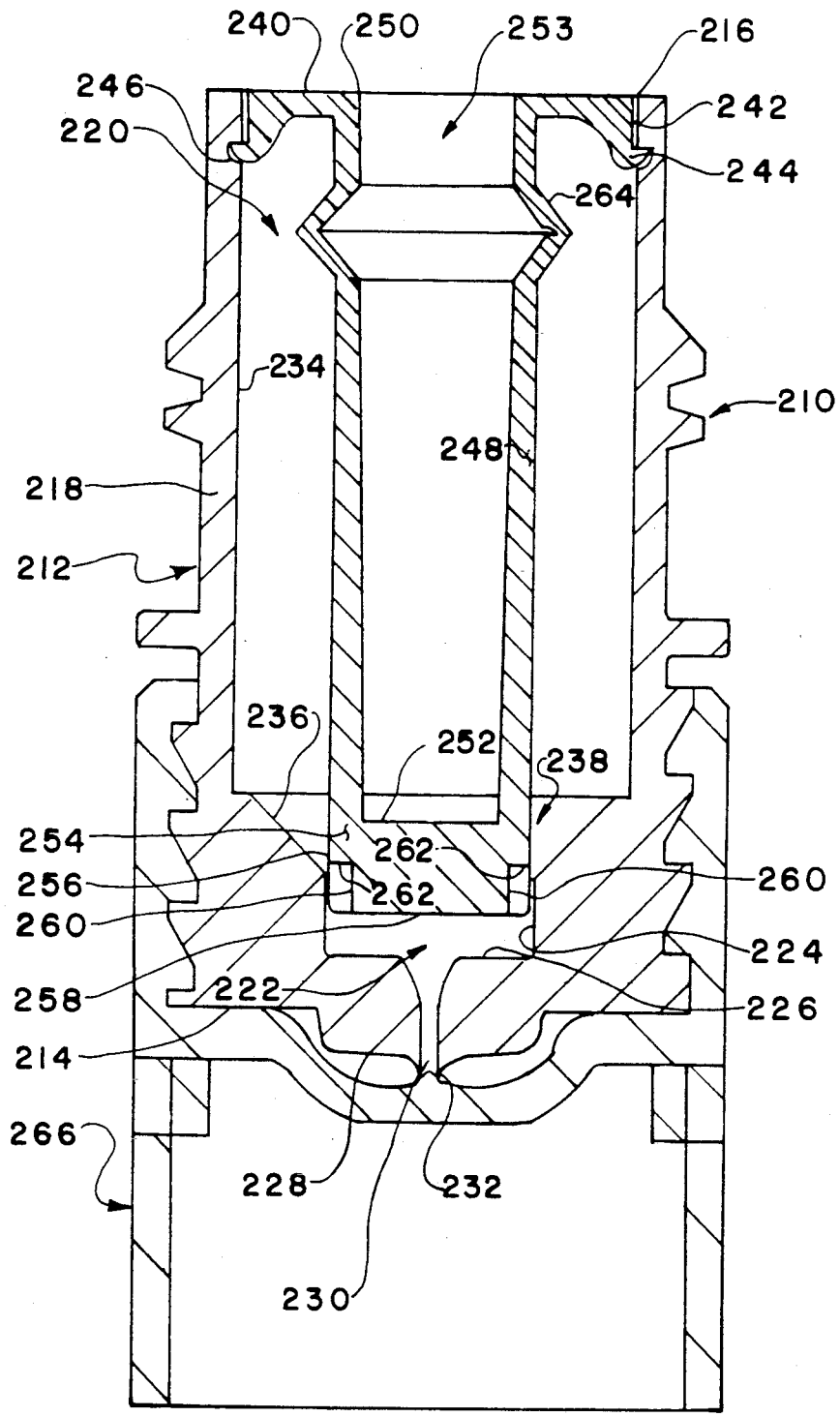
FIG. 3 is a cross-sectional view of a third embodiment of an ocular treatment apparatus embodying the invention.

Turning to FIG. 3, another embodiment of the ocular treatment apparatus of the invention is indicated generally by the reference numeral 210. The apparatus 210 comprises a body illustrated generally as 212. The body 212 comprises a closed end 214, an open end 216, and a generally cylindrical shaped wall 218. The body 212 also defines a cavity 220 for holding medicament, and a drop cavity 222 in fluid communication with the cavity 220. The drop cavity 222 is defined by a cylindrical shaped surface 224, and a flat base surface 226, both formed in the closed end 214 of the body. The body 212 also comprises a raised nozzle 228 formed on an exterior face of the closed end 214. The nozzle 228 defines a nozzle orifice 230 which is coaxial with the body 212. The nozzle orifice 230 is formed through a raised tip 232 of the nozzle and extends in the axial direction of the apparatus into the drop cavity 222. As shown in FIG. 3, the nozzle orifice 230 flares open into the base 226 of the drop cavity in order to induce the flow of medicament into the nozzle orifice.

The body 212 further defines a cylindrical shaped interior surface 234, extending from the open end 216 of the body, and along a substantial portion of its axial length. A sloped surface 236 of the body extends inwardly from the base of the surface 234 to the cylindrical surface 224 of the drop cavity. The slope of the surface 236 induces the flow of medicament from the cavity 220 into the drop cavity 222.

The apparatus 210 further comprises a piston member illustrated generally as 238. The piston member 238 comprises a flange 240 having a peripheral surface 242 dimensioned, as shown in FIG. 3, to be slideably engaged within the cylindrical surface 234 of the body. The piston member 238 further comprises a peripheral lobe 244 formed adjacent an edge of the surface 242. The lobe 244 is dimensioned to be received within a peripheral recess 246 formed within the cylindrical surface 234 of the body 212. The piston member 238 is connected to the body 212 by pressing the flange 240 into the open end 216 of the body, until the lobe 244 snaps into the peripheral recess 246. When the lobe 244 is seated within the recess 246, the lobe forms a substantially fluid tight seal between the piston member 238 and the body 212. The piston member 238 further comprises a substantially cylindrical wall 248, coaxial with the apparatus 210, and extending inwardly from an opening 250 formed in the flange 240. The wall 248 defines on one end thereof a closed end 252, thus defining an open cavity 253 within the wall 248. The closed end 252 of the piston member is formed into a piston head 254, having a substantially cylindrical shaped side surface 256, and flat bottom surface 258. The surface 256 is dimensioned, as shown in FIG. 3, to be slideably engaged within the wall 224 of the drop cavity 222. The piston member further defines several elongated grooves 260, 260 formed within the surface 256, and extending inwardly from the top surface 258 of the piston head. Each groove 260, 260 extends in the axial direction of the piston head and defines a closed end 262, 262. The piston member 238 further comprises an accordion section 264 formed within the wall 248. The accordion section allows the piston member 238 to be moved relative to the body 212 in the axial direction of the apparatus, so that the piston head 254 can be slideably engaged within the drop cavity 222. As can be seen, because the accordion section 264 deforms upon movement of the piston member 238, the overall volume of the cavity 220 and drop cavity 222 does not change when the piston member is depressed. Accordingly, there is no noticeable change in pressure within the cavity 220 when the piston member 238 is depressed.

The apparatus 210 further comprises a cap 266 which may be threadedly engaged with the body 212 to cover the nozzle orifice 230. The cap 266 may be the same as the caps 16 and 116 described above in relation to the previous embodiments.

In the operation of the apparatus 210, a substantially predetermined volume of medicament is released from the apparatus by depressing the piston member 238 so that the piston head 254 is pressed into the drop cavity 222. The piston member 238 may be depressed by employing, for example, a cover and piston rod (not shown) as described above in relation to the previous embodiment and illustrated in FIG. 2. As will be evident to those skilled in the art, the piston rod is dimensioned to fit within the cavity 253, so that the end of the piston rod can be abutted against the surface 252 for depressing the piston member 238. When the surface 258 of the piston head engages the bottom surface 226 of the drop cavity, a single drop of medicament is displaced through the nozzle orifice 230 for release into the eye. The volume of each drop of medicament is substantially equal to the volume of the drop cavity 222 below the piston head 254, when the piston head is depressed far enough so that the closed ends 262, 262 of the grooves are located immediately below the opening into the drop cavity. This volume is preferably equal to about 20 microliters. When the pressure is released from the piston member 238, the tension in the accordion section 264, which is stretched when the piston member is depressed, drives the piston head 254 upwardly into its normal position above the drop cavity.

Turning to FIGS. 4 through 8, another embodiment of the ocular treatment apparatus of the invention is indicated generally by the reference numeral 310. The apparatus 310 is provided preferably for use with medicaments that require two separate solutions to be mixed into one homogeneous solution prior to application of the medicament into the eye.

Figures 4, 5:
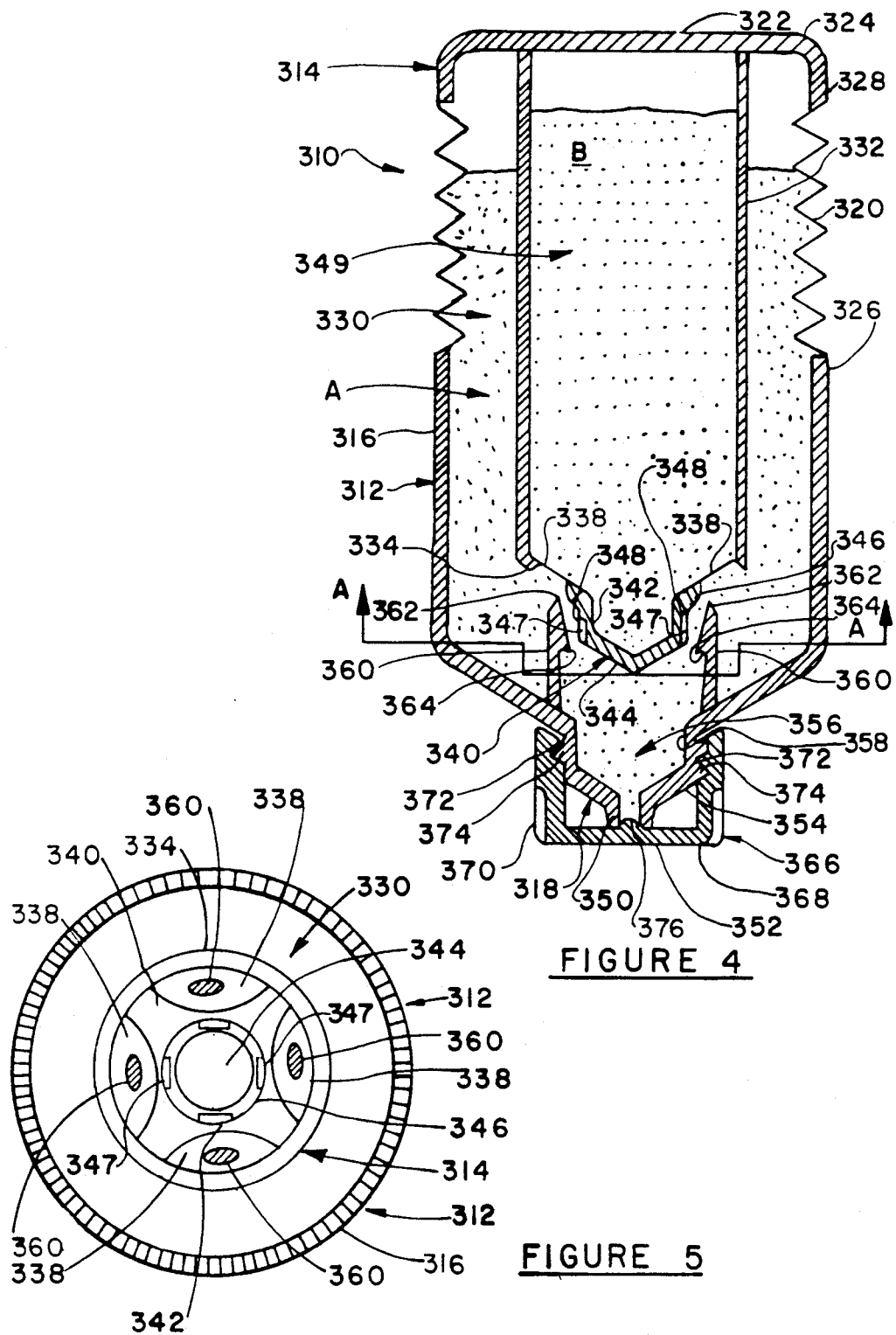
FIG. 4 is a cross-sectional view of a fourth embodiment of an ocular treatment apparatus embodying the invention for use preferably with medicaments that require mixing of two separate solutions or compounds prior to use.
FIG. 5 is a bottom cross-sectional view of part of the ocular treatment apparatus of FIG. 4 taken along the line A—A.

The apparatus 310 comprises generally an outer shell 312 and an inner shell 314. The outer shell 312 comprises a cylindrical shaped wall 316, a nozzle 318, and a generally cylindrical shaped accordion section 320. The inner shell 314 comprises a closed end 322 having a peripheral flange 324 which is curved inwardly in the axial direction of the apparatus. One end of the accordion section 320 is joined to the wall 316 of the outer shell by means of a fluid tight peripheral joint 326. The other end of the accordion section 320 is joined to the flange 324 of the inner shell by means of a fluid tight peripheral joint 328. The joints 326 and 328 are formed in a manner known to those skilled in the art, such as by ultrasonic welding. The accordion section 320 thus permits the inner shell 314 to be depressed relative to the outer shell 312 in the axial direction of the apparatus, as will be described further below. As shown in FIG. 4, the outer shell 312 and the inner shell 314 define therebetween a first fluid cavity 330 for holding a first solution of medicament, indicated as A.

The inner shell 314 further comprises a generally cylindrical shaped wall 332 extending inwardly from the closed end 322 and in the axial direction of the apparatus. The wall 332 is dimensioned, as shown in FIG. 4, to fit within the wall 316 of the outer shell 312. The other end of the wall 332 is formed into an annular edge 334. The annular edge 334 is, in turn, joined to the outer peripheral edge of a wall 336 of the inner shell, as shown best in FIG. 5. The wall 336 defines four thin-walled sections 338, 338, equally spaced within the wall 336, and which may be broken to permit the flow of medicament therethrough, as will be described further below.

The inner peripheral edge of the wall 336 is joined to a piston head, indicated generally as 340, of the inner shell. The piston head 340 is defined by a generally cylindrical shaped side wall 342, coaxial with the apparatus, and a sloped bottom wall 344. As shown in FIG. 4, the wall 344 slopes upwardly from the axial center of the piston head. The piston head further comprises a flange 346, formed along the upper edge of the wall 342, and joined to the inner edge of the wall 336. The piston head also preferably defines several axially elongated grooves, shown typically as 347, 347, defined within the outer surface of the cylindrical shaped wall 342. Each groove 347, 347 extends upwardly from the corner of the bottom wall 344 and defines a closed end 348, 348. As shown in FIG. 4, the inner shell 314 defines within the cylindrical wall 332 a second fluid cavity 349, isolated from the first cavity 330, for holding a second solution of medicament, indicated as B.

The nozzle 318 of the outer shell defines a raised tip 350 having a nozzle orifice 352 formed therethrough and coaxial with the apparatus. The nozzle orifice 352 extends through a top wall 354 of the nozzle, and is in fluid communication with a drop cavity 356. The drop cavity 356 is defined by the top wall 354, and a generally cylindrical shaped side wall 358 of the nozzle. The drop cavity 356 is, in turn, in fluid communication with the first fluid cavity 330. As shown in FIG. 4, the top wall 354 of the nozzle slopes upwardly from the axial center of the nozzle at substantially the same angle as the wall 344 of the piston head. Likewise, the inner diameter of the wall 358 of the nozzle is dimensioned slightly larger than the outer diameter of the wall 342 of the piston head, so that the piston head may be slideably engaged within the drop cavity 356.

The outer shell 312 further comprises four pins 360, 360, as shown in FIGS. 4 and 5, extending inwardly from the wall 316 of the outer shell and in the axial direction of the apparatus. The pins 360, 360 are equally spaced adjacent the edge of the drop cavity 356 and each are located, respectively, below one of the thin-walled sections 338, 338 of the inner shell. Each pin 360 defines a pointed tip 362, and a lip 364 extending inwardly from an interior side thereof. As shown in FIG. 4, the distance between each opposing pair of tips 362, 362 is slightly greater than the outer diameter of the flange 346 of the piston head. However, the distance between the lips 364, 364 of the pins is slightly less than the outer diameter of the flange 346.

Figure 6:
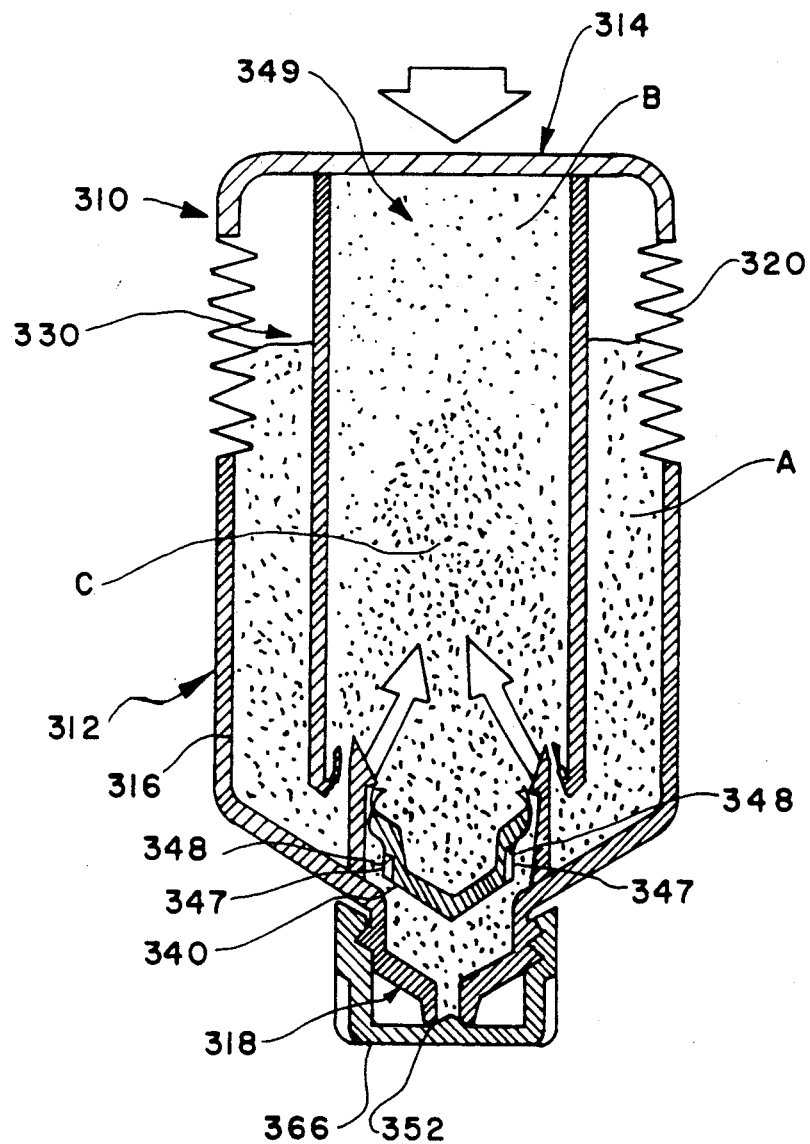
FIG. 6 is a cross-sectional view of the ocular treatment apparatus of FIG. 4, illustrating the operation of the apparatus when mixing two separate solutions of medicament contained within the apparatus.

In operating the apparatus 310 to mix the separate solutions of medicament A and B, the inner shell 314 is moved inwardly so that the piston head 340 is depressed toward the drop cavity 356. As the piston head is depressed, the flange 346 of the piston head engages the interior surface of each pin 360, 360. As the piston head is further depressed, the tips 362, 362 of the pins each engage and break the respective thin-walled sections 338, 338 of the inner shell, as shown in FIG. 6. Then, as the piston head 340 is further depressed, the pins 360, 360 further tear open the thin-walled sections 338, 338. The medicament A within the first cavity 330 then flows through the broken sections 338, 338 and mixes with the medicament B within the second cavity 349, as indicated by the arrows shown in FIG. 6. The mixture of the medicaments A and B forms a homogeneous medicament, indicated as C.

Figures 7, 8:
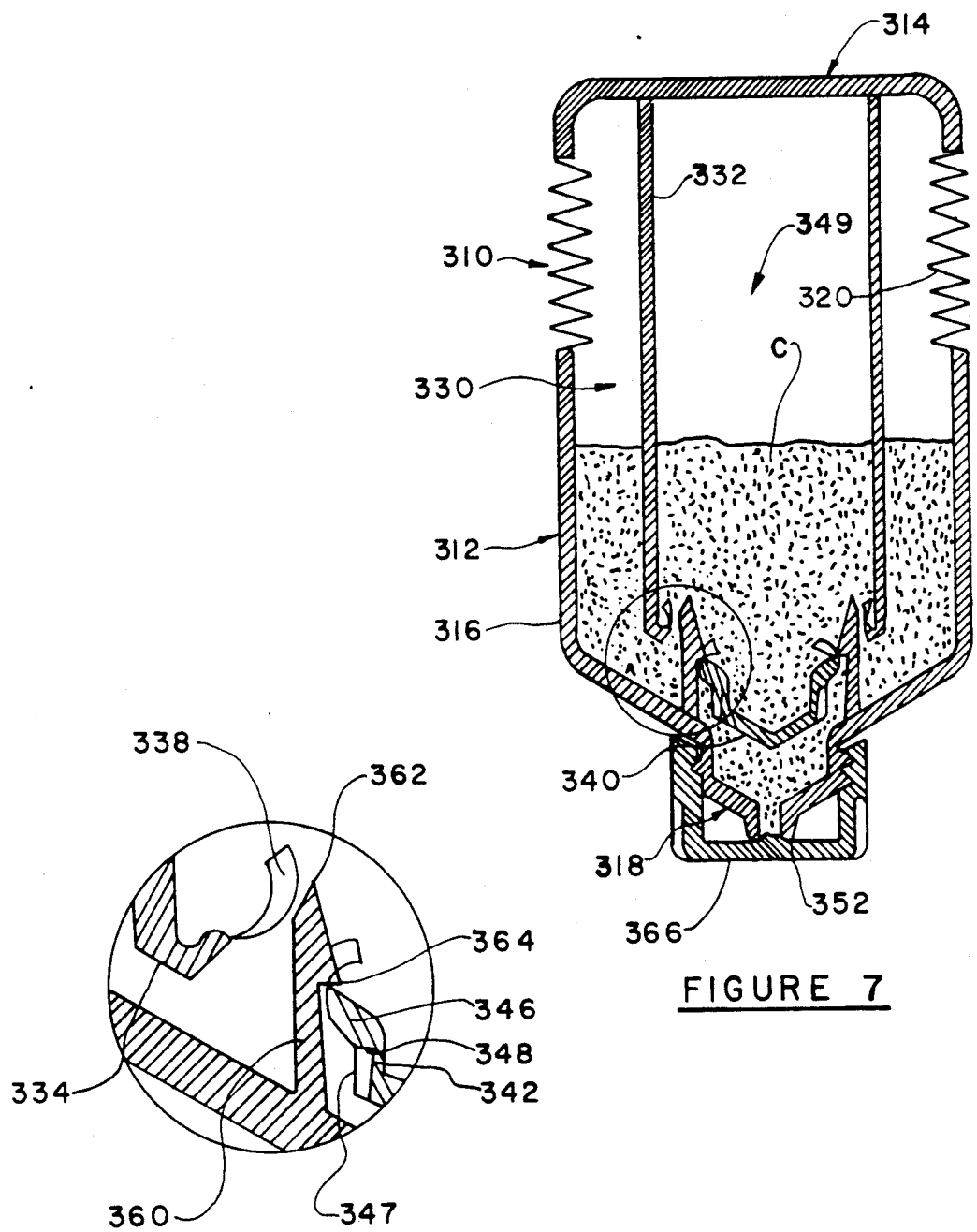
FIG. 7 is a cross-sectional view of the ocular treatment apparatus of FIG. 4, illustrating the apparatus after two separate solutions contained within the apparatus are mixed into one homogeneous solution of medicament.
FIG. 8 is a magnified view of a portion of the ocular treatment apparatus of FIG. 7, illustrating the inner cavity of the apparatus pierced in order to permit the two solutions of medicament to be mixed.

Upon breaking the thin-walled sections 338, 338, as the piston head 340 is further depressed, the flange 346 is slideably engaged against the pins 360, 360 so as to bend the pins outwardly. However, when the flange 346 is pressed through the lips 364, 364, the pins 360, 360 flex back toward their initial position so that the lips are positioned beneath the flange 346 of the piston head, as shown in FIGS. 7 and 8. The lips 364, 364 of each pin 360, 360 then retain the piston head 340 within the pins, so that the piston head cannot be driven back to its initial position above the pins. The user may then shake the apparatus 310 to allow the first and second solutions of medicament to completely mix into one homogeneous medicament C, as shown in FIG. 7.

One feature of the invention is that the second fluid tight cavity 349 may be evacuated to a subatmospheric pressure after it is filled with the second medicament B. Accordingly, when the thin-walled sections 338, 338 are pierced by the pins 360, 360, the pressure differential between the first cavity 330 and second cavity 349, causes the first medicament A to be sucked into the cavity 349 and to mix with the second medicament B. The user, therefore, is not required to thoroughly shake the apparatus to mix the two solutions of medicament, but rather, the pressure differential between the first and second cavities alone forces the medicaments to mix into one homogeneous medicament C.

After mixing the homogenous medicament C, the user may then release a substantially predetermined volume of medicament into the eye. The user simply aims the nozzle tip 350 over the eye and presses the inner shell 314 toward the nozzle, as indicated by the arrow shown in FIG. 6. The piston head 340 of the inner shell is then slideably depressed into the drop cavity 356 and, in turn, displaces the medicament C within the drop cavity through the nozzle orifice 352, for release in the eye. The grooves 348, 348 of the piston head permit any excess medicament or air within the drop cavity 356 to flow upwardly into the cavity 330 and not into the drop of medicament. The volume of each drop is controlled by appropriately dimensioning the drop cavity 356 and piston head 340. Accordingly, the volume of a drop is substantially equal to the volume of space within the drop cavity, when the piston head 340 is depressed far enough so that the closed ends 348, 348 of the grooves 347, 347 of the piston head are moved immediately below the opening of the drop cavity 356. This volume is preferably equal to about 20 microliters. When the user releases the pressure from the inner shell 314, the spring force in the accordion section 320, which is compressed when the inner shell is depressed, drives the piston head 340 upwardly until it is stopped against the lips 364, 364 of the pins 360, 360. As can be seen, the stroke of the piston head 340 is constant and is limited by the lips 364, 364 of the pins. The medicament within the cavity 330 then flows beneath the piston head and fills the drop cavity 356. The inner shell 314 may then be depressed to release another drop of medicament.

The apparatus 310 further comprises a cap 366 having a closed end 368, and a cylindrical shaped side wall 370. The side wall 370 has formed on its interior surface threads 372, 372, which, as shown in FIG. 4, are dimensioned to mate with threads 374, 374 formed on the exterior surface of the wall 358 of the nozzle. The cap 366 further comprises a nipple 376, formed on the axial center of the interior surface of the closed end 368. When the cap 366 is threaded onto the nozzle, the nipple 376 is rotated over the nozzle orifice 352 and closes the orifice, and thus prevents any medicament from leaking therefrom.

As will be evident to those skilled in the art, the apparatus 310 may be employed with other ocular apparatus, such as the apparatus disclosed in U.S. patent application No. 07/276,526, incorporated herein by reference above, that may properly orient the apparatus 310 over the eye and/or evert the lower eyelid when a drop of medicament is released into the eye. Accordingly, the apparatus 310 may be further provided with flanges (not shown) similar to the flanges 74, 74 described above in relation to FIG. 1, or other such means for mounting the apparatus 310 within other ocular apparatus.

What is claimed is:

1. An ocular treatment apparatus for applying medicament into an eye, said apparatus comprising:
    a nozzle having an orifice defined therein for releasing medicament into the eye;
    storage means including a storage cavity in fluid communication with said nozzle orifice for holding medicament for release into the eye;
    a vial defining a first cavity for holding a first medicament, said first cavity being in fluid communication with said storage cavity, said vial further defining a second cavity for holding a second medicament;
    means for controllably placing said first cavity of said vial in fluid communication with said second cavity of said vial for mixing in said storage cavity the first and second medicaments into a mixed medicament; and
    displacement means for displacing a substantially predetermined volume of mixed medicament within said storage cavity through said nozzle orifice for release into the eye.

2. An ocular treatment apparatus as defined in claim 1, wherein
    said displacement means comprises a piston member, said piston member being engageable within said storage cavity for displacing mixed medicament through said nozzle orifice for release into the eye.

3. An ocular treatment apparatus as defined in claim 1, wherein
    said displacement means includes a piston member, said piston member being engageable within said storage cavity for displacing medicament within said storage cavity through said nozzle orifice for release into the eye.

4. An ocular treatment apparatus as defined in claim 1, wherein
    said displacement means displaces a single drop of medicament each time said displacement means displaces medicament within said storage means, through said nozzle orifice, for release into the eye.

5. An ocular treatment apparatus for applying medicament into an eye, said apparatus comprising:
    a nozzle having an orifice defined therein for releasing medicament into the eye and defining a nozzle cavity coupled in fluid communication with said orifice for receiving medicament for release into the eye;
    a vial including an outer shell and an inner shell, said inner shell being joined to said outer shell and moveable relative thereto, said outer shell defining a first cavity for holding a first medicament, said first cavity being in fluid communication with said nozzle cavity, and said inner shell defining a second cavity for holding a second medicament;
    means for controllably placing said first cavity of said vial in fluid communication with said second cavity of said vial for mixing in said nozzle cavity the first and second medicaments into a mixed medicament; and
    displacement means for displacing a substantially predetermined volume of mixed medicament within said nozzle cavity through said nozzle orifice for release into the eye, said displacement means including a piston member coupled to said inner shell and engageable within said nozzle cavity by depressing said inner shell relative to said outer shell for displacing medicament within said nozzle cavity through said nozzle orifice for release into the eye.

6. An ocular treatment apparatus as defined in claim 5, wherein said means for controllably placing said first and second cavities of said vial in fluid communication comprises:
    at least one pin member, said pin member protruding inwardly from an interior surface of said outer shell such that when said inner shell is depressed relative to said outer shell, said pin member pierces a wall defining said second cavity for holding a second medicament, thus placing said first and second cavities in fluid communication for mixing the first and second medicaments into a mixed medicament.

7. An ocular treatment apparatus for applying medicament into an eye, said apparatus comprising:
    a nozzle having an orifice defined therein for releasing medicament into the eye;
    storage means in fluid communication with said nozzle orifice for holding medicament for release into the eye;

a vial defining a first cavity for holding a first medicament, said first cavity being in fluid communication with said storage means, said vial further defining a second cavity for holding a second medicament;

means for controllably placing said first cavity of said vial in fluid communication with said second cavity of said vial for mixing in said storage means the first and second medicaments into a mixed medicament, wherein said second cavity for holding the second medicament is evacuated to a subatmospheric pressure for facilitating the mixing of the first and second medicaments; and displacement means for displacing a substantially predetermined volume of mixed medicament with said storage means through said nozzle orifice for release into the eye.

8. An ocular treatment apparatus for applying medicament into an eye, comprising:

a nozzle defining an orifice for releasing medicament into the eye;

storage means in fluid communication with said nozzle orifice for holding medicament for release into the eye;

displacement means for displacing a substantially predetermined volume of medicament within said storage means through said nozzle orifice for release into the eye;

a body, said body defining a first cavity for holding a first medicament, said first cavity being in fluid communication with said storage means, said body further defining a second cavity for holding a second medicament wherein said body defines a first shell and a second shell, said second shell being joined to said first shell and movable relative thereto, said first and second shells defining therebetween said first cavity for holding a first medicament, and said second shell defining said second cavity for holding a second medicament; and means for controllably placing said first cavity of said body in fluid communication with said second cavity of said body for mixing in said storage means the first and second medicaments into a mixed medicament solution.

9. An ocular treatment apparatus as defined in claim 8, wherein said displacement means comprises a piston member, said piston member being engageable within said storage means for displacing medicament through said nozzle orifice.

10. An ocular treatment apparatus as defined in claim 9, wherein said piston member is suspended from said second shell and within said first shell, said piston member being engageable within said storage means by moving said second shell relative to said first shell for displacing medicament through said nozzle orifice.

11. An ocular treatment apparatus as defined in claim 8, wherein said means for controllably placing said first cavity and said second cavity of said body in fluid communication includes:

at least one pin member, said pin member protruding inwardly from an interior surface of said first shell such that when said second shell is moved relative to said first shell, said pin member pierces a wall defining said second cavity, thus placing said first and second cavities in fluid communication for mixing the first and second medicaments into a mixed medicament.

12. An ocular treatment apparatus for applying medicament into an eye, said apparatus comprising:

a nozzle defining an orifice for releasing medicament into the eye;

a storage portion coupled in fluid communication with said nozzle orifice for holding medicament for release into the eye;

a body member defining a first cavity for holding a first medicament, said first cavity being in fluid communication with said storage portion, said body further defining a second cavity for holding a second medicament;

means for placing said first cavity of said body member in fluid communication with said second cavity of said body member for mixing in said storage portion the first and second medicaments into a mixed medicament solution; and a piston member for displacing a substantially predetermined volume of medicament within said storage portion through said nozzle orifice for release into the eye.

13. An ocular treatment apparatus as defined in claim 12, wherein said storage portion includes a nozzle cavity defined within said nozzle, said nozzle cavity being in fluid communication with both said nozzle orifice and with said first cavity of said body member, said piston member being engageable within said nozzle cavity for displacing medicament therein through said nozzle orifice for release into the eye.

14. An ocular treatment apparatus as defined in claim 12, wherein said body member includes a first portion defining said first cavity and a second portion defining said second cavity, said first and second portions being movable relative to each other.

15. An ocular treatment apparatus as defined in claim 14, wherein said piston member is coupled to said first portion and movable with said first portion relative to said second portion for displacing a substantially predetermined volume of medicament from said storage portion.

16. An ocular treatment apparatus as defined in claim 12, wherein said means for placing said first cavity in fluid communication with said second cavity includes a piercing member for piercing a wall defining at least one of said cavities to couple said first and second cavities in fluid communication.

* * * * *